United States Patent [19]

Loucks

[11] Patent Number: 4,983,528
[45] Date of Patent: Jan. 8, 1991

[54] MEASUREMENT OF UNSATURATION LEVEL IN BUTYL AND EPDM RUBBERS

[75] Inventor: Dennis A. Loucks, Bright's Grove, Canada

[73] Assignee: Polysar Limited, Sarnia, Canada

[21] Appl. No.: 362,335

[22] Filed: Jun. 6, 1989

[51] Int. Cl.$^5$ ............................................ G01N 21/00
[52] U.S. Cl. .................................... 436/141; 436/142; 436/85; 436/161; 422/70; 73/611 C; 210/198.2; 210/656
[58] Field of Search ................. 436/141, 142, 85, 161; 422/70, 68; 73/61.1 C; 210/198.2, 656

[56] References Cited

U.S. PATENT DOCUMENTS 4,728,344 3/1988 Stacy ........................................ 55/67

OTHER PUBLICATIONS

Harrison et al, "Aging of Pressure Sensitive Adhesives, II: Use of Multi-Detector Sec", Journal of Liquid Chromatography, vol. 6, pp. 2723-2737 (1983).
Grinshpun et al, "SEC of Copolymers", Polymeric Materials in Science and Engineering, vol. 54, pp. 174-179 (1986).
Del Rios, "Characterization of Polymers and Additives Utilizing a New Differential Refractometer and Absorbance Detector", Paper No. 346, Pittsburgh Conference and Exposition, Mar. 1986.
Kohn, "Size Exclusion Chromatography (XII) Analysis of Silicon-Phenyl Groups in Molecuylar Weight Components of Polydimethylsiloxanes", U.S. Government Report DE 86015001, Aug. 1986.

Primary Examiner—Robert J. Warden
Assistant Examiner—David Redding
Attorney, Agent, or Firm—Stevens, Davis, Miller & Mosher

[57] ABSTRACT

A method is provided for quantitatively determining the amount of unsaturation in butyl and EPDM rubbers using a gel permeation chromatograph in combination with an ultraviolet detector. Placement of a differential refractive index detector in series with said ultraviolet detector provides a method for the simultaneous measurement of the amount of unsaturation, the molecular weight distribution and the amount of antioxidant in said rubbers.

12 Claims, No Drawings

MEASUREMENT OF UNSATURATION LEVEL IN BUTYL AND EPDM RUBBERS

FIELD OF THE INVENTION

The present invention relates to a method for quantitatively determining the amount of unsaturation in unsaturated elastomeric interpolymers of at least one monoolefin and one diolefin selected from the group consisting of butyl rubbers and ethylene-propylene-nonconjugated diene terpolymers. The present invention also provides a method for the simultaneous measurement of the amount of u saturation, the molecular weight distribution and the amount of antioxidant in said unsaturated elastomeric interpolymers.

BACKGROUND OF THE INVENTION

The physical properties and processability of a rubber are key performance areas that the commercial rubber producer has to monitor. Amongst these are the level of unsaturation, the molecular weight distribution, the amount of ultraviolet stabilizer, the amount of antioxidant and the amount of plasticizer. Traditionally each of these parameters has been analyzed by an individual method and often this has proven to be difficult because the parameter is present at such a low concentration level.

The Iodine Index is presently accepted by the rubber industry as the method for determining the amount of unsaturation in an unsaturated rubbery copolymer such as a butyl rubber. However the method is not universally applicable to the quantitative determination of the level of unsaturation in a number of unsaturated rubbery copolymers as the amount of iodine that adds to each of the various isomeric olefinic structures in said unsaturated rubbery copolymers is not known. The method is further deficient in that it is operator dependent, it takes several hours to perform and other unsaturated species such as oligomers, ultraviolet stabilizer and antioxidant present in the sample of unsaturated rubbery copolymer submitted for analysis will, if not extracted, add to the final unsaturation value.

Analysis by nuclear magnetic resonance spectrometry of unsaturated rubbery copolymers in which the level of unsaturation is relatively high is possible. However nuclear magnetic resonance spectrometry is not capable of providing accurate unsaturation data on polymers with less than about three weight percent unsaturation as the instrument is not sufficiently sensitive. Moreover the cost of the instrument is such that the average rubber producer would not be prepared to install it in a quality control laboratory.

Hence there is a need in the industry for a method which is both rapid and accurate over a wide concentration range. Furthermore it would be advantageous if such a method could be placed in combination with at least one of the methods presently in use for the determination of one or more of the other parameters, as the cost of the analyses to the rubber producer would be reduced considerably.

To the best of Applicant's knowledge there is no report of an analytical method which is capable of measuring simultaneously the unsaturation level, the antioxidant level and the molecular weight distribution of an unsaturated elastomeric interpolymer selected from the group consisting of butyl rubbers and ethylene-propylene-nonconjugated nonconjugated diene terpolymers.

There are a number of patents which disclose the use of gel permeation chromatographs in combination with an appropriate detection system in the characterization of polymers. For example, U.S. Pat. No. 4,728,344 discloses the use of a gel permeation chromatograph in which the columns and, preferably the detector are heated, for determining the relative concentration and molecular weight of a component in a polymer which is soluble only above about 150° C. However the Patent does not suggest using such a device to detect and quantify the unsaturation level in unsaturated elastomeric interpolymers nor does the Patent suggest that by placing a differential refractometer and a variable wavelength ultraviolet detector in series with the gel permeation chromatograph that it would be possible to measure simultaneously the unsaturation level, the antioxidant level and the molecular weight distribution of an unsaturated elastomeric interpolymer of one or more monoolefins and a diolefin.

Harrison, Yates and Johnson in the Journal of Liquid Chromatography, Volume 6, pages 2723-37 (1983) described the use of a gel permeation chromatograph in combination with a differential refractometer and an ultraviolet detector for a study of the aging of pressure-sensitive adhesive films based on isoprene-styrene block copolymers. The carbonyl chromophore formed on the room temperature oxidation of the thin films was monitored by the ultraviolet detector while the molecular weight distribution was measured with the differential refractometer. It was not suggested, however, that this system could be employed for the analysis of the molecular weight distribution and the amount of unsaturation in unsaturated elastomeric interpolymers of at least one monoolefin and a diolefin.

Grinshpun and Rudin described in Polymeric Materials in Science and Engineering, Volume 54 pages 174-179 (1986), the use of a gel permeation chromatograph in combination with three different detectors to study the molecular weight distributions of a series of ethylene-propylene-nonconjugated diene terpolymers having different amounts of unsaturation. The levels of unsaturation o the terpolymers, however, were to the best of Applicant's knowledge not determined using an ultraviolet detector in combination with the gel permeation chromatograph.

Kohn in U.S. Government Report DE86015001 describes methods for the identification and quantification of phenyl groups in molecular weight components of polydimethyl-siloxane prepolymers which utilize on-line differential refractometer, infrared and ultraviolet detection during gel permeation chromatographic separation. For the quantification of the phenyl groups it was found that a more polar solvent such as tetrahydrofuran or 1,4-dioxane which apparently complexes with the phenyl groups giving rise to enhanced absorbances that are less dependent on the position of the phenyl groups, is required.

Del Rios in paper No. 346 at the Pittsburgh Conference and Exposition, March 1986, focused on the use of a differential refractometer and an ultraviolet detector in series with a gel permeation chromatograph for determining the molecular weight distribution of a polymer together with the low molecular weight additives present in it. No reference was made to the possibility of analyzing the unsaturation content of unsaturated elastomeric interpolymers.

SUMMARY OF THE INVENTION

The present invention provides a method for determining the amount of unsaturation in an unsaturated elastomeric interpolymer of at least one monoolefin and one diolefin selected from the group consisting of butyl rubbers and ethylene propylene-nonconjugated diene rubbers, said method comprising:
 (i) dissolving a known weight of said unsaturated elastomeric interpolymer in a measured volume of a suitable solvent;
 (ii) passing a sample of the resulting solution through a gel permeation chromatograph in which three or more chromatographic columns comprise columns of porous particles of cross-linked polymeric material, said porous particles having a diameter of about 4 microns to about 11 microns and a pore size in the range of $10^2$ angstrom to $10^6$ angstrom and
 (iii) detecting and quantifying the amount of unsaturation in said unsaturated elastomeric interpolymer as it is eluted from said chromatographic column.

DETAILED DESCRIPTION OF THE INVENTION

The polymers which may be analyzed in accordance with the method of the present invention include butyl rubbers and ethylene-propylene-nonconjugated diene rubbers. Absorption of short wavelength electromagnetic radiation by the isolated ethylenic chromophore almost always occurs in the far ultraviolet region which is not readily accessible due to the fact that atmospheric absorption occurs in this region. However substitution of the hydrogen atoms by alkyl groups moves the absorption to longer wavelengths. As a consequence the residual nonconjugated unsaturation in both butyl rubbers and ethylene-propylene-nonconjugated diene rubbers is rendered accessible to analysis by ultraviolet spectrometry. Any low molecular weight species such as oligomers, ultraviolet stabilizers, antioxidants and the like which may have chromophores that also absorb in the same region of the ultraviolet spectrum as said butyl rubbers and ethylene propylene-nonconjugated diene rubbers and thus would interfere with the analysis are first separated by gel permeation chromatography.

The unsaturated elastomeric interpolymer of at least one monoolefin and one diolefin is dissolved in a suitable solvent. The solvent must meet two criteria in that the solvent must be capable of dissolving said unsaturated elastomeric interpolymer and at the same time the solvent must also be transparent to ultraviolet radiation down to about 210 nanometres. The preferred solvents include tetrahydrofuran that does not contain preservative, cyclohexane and hexane, tetrahydrofuran that does not contain preservative being particularly preferred.

The solution of unsaturated elastomeric interpolymer is prepared in a very dilute form. Preferably less than 0.5, most preferably 0.2 W/V percent of sample is dissolved in the solvent. Very small samples of the resulting solution, preferably less than 500 ul, most preferably 200 ul are analyzed using the gel permeation chromatograph on-line with a suitable detector or combination of detectors.

The chromatographic columns used in accordance with this invention contain porous particles of cross-linked polymeric material, usually cross-linked poly(styrene-divinylbenzene) said particles having a diameter of about 4 microns to about 11 microns and a pore size in the range $10^2$ angstrom to $10^6$ angstrom. In a preferred embodiment a series of three columns is used in which each column is packed with a cross-linked poly(styrene-divinylbenzene) material the particles of which have a diameter of about 4 microns to about 6 microns and a range of pore size of from about $10^2$ angstrom to about $10^6$ angstrom. Columns of this type are commercially available from Polymer Laboratories. In another embodiment it is preferred to use a series of four columns in which each column is packed with porous particles of cross-linked polymeric material the diameter of which are the same but the pore size of which differ from that of the porous particles in the adjacent columns. A particularly useful series of columns comprises a series of four columns packed with porous particles of cross-linked poly(styrene-divinylbenzene) that have a diameter of about 4 microns to about 6 microns. The first column is packed with said porous particles that have a pore size of about $10^3$ angstrom, the second column is packed with said porous particles that have a pore size of about $10^4$ angstrom, the third column is packed with said porous particles that have a pore size of about $10^5$ angstrom and the fourth column is packed with said porous particles that have a pore size of about $10^6$ angstrom. Commercially available columns of this type are Waters Ultrastyragel columns.

When the sample of the solution of unsaturated elastomeric interpolymer passes through the columns, it is separated by molecular size. The largest molecules pass through the columns fastest and the smallest molecules pass through the columns slowest. Thus, the polymer molecules will exit the chromatographic columns first and the larger the molecular weight of the polymer molecule, the sooner it is eluted from the columns. The low molecular weight species such as oligomers, ultraviolet stabilizer and antioxidant will exit the chromatographic columns last according to their respective molecular weights. At the exit from the columns there is a suitable detector. Preferably the detector comprises an ultraviolet detector. Preferably the detector comprises an ultraviolet detector operated at a wavelength of about 217 nanometres to about 222 nanometres, a suitable ultraviolet detector being the Waters 481 ultraviolet detector. The detector should be used in conjunction with a quantifying means. Preferably the signal from the ultraviolet detector is digitized and fed to a computer which then generates a graph of the amount of unsaturation in the unsaturated elastomeric interpolymer passing through the chromatographic columns with the area under the graph being proportional to the relative amount of unsaturation in the elastomeric interpolymer in the sample. Preferably the computer will integrate the area under the graph. Suitable computers and software are available, a useful computer software package being the Waters GPC Software Version 4.0 marketed by the Waters Company.

The method of the present invention further comprises a means whereby the amount of unsaturation, the molecular weight distribution and the amount of antioxidant in the unsaturated elastomeric interpolymer are simultaneously detected and quantified. In said method at the exit from the chromatographic columns there are connected in series a suitable ultraviolet detector and a differential refractive index detector in order that as the unsaturated elastomeric interpolymer molecules exits the chromatographic columns the amount of unsaturation in said polymer molecules is detected by said ultraviolet detector and the molecular weight distribution of said polymer molecules is detected by said differential refractive index detector. The antioxidant initially present in said unsaturated elastomeric interpolymer is eluted later from the chromatographic columns, it is detected by said ultraviolet detector. Preferably the ultraviolet detector comprises a multichannel, multiwavelength ultraviolet detector operated at a wavelength of about 217 nanometres to about 222 nanometres and at a wavelength of about 275 nanometres to about 285 nanometres. A suitable ultraviolet detector is the Waters 490 programmable detector and a suitable differential refractive index detector is the Waters 410 differential refractive index detector. Both the ultraviolet detector and the differential refractive index detector should be used in conjunction with a quantifying means. Preferably the signals from the ultraviolet detector and the signal from the differential refractive index detector are digitized and fed to a computer which then generates a graph of the amount of unsaturation and a graph of the molecular weight distribution in the unsaturated elastomeric interpolymer passing through the chromatographic columns and a graph of the amount of antioxidant initially present in the unsaturated elastomeric interpolymer, the areas under the graphs being proportional to the relative amount of unsaturation and the relative molecular weight distribution in the elastomeric interpolymer and the relative amount of antioxidant initially present in the elastomeric interpolymer. Preferably the computer will integrate the areas under the respective graphs. Suitable computers and software are available, a useful computer software package being the Waters GPC Software Version 4.0 marketed by the Waters Company.

Determination of the absolute amount of unsaturation in the unsaturated elastomeric interpolymer may be made by comparing the area under the graph resulting from the absorbance of ultraviolet radiation at about 217 nanometres to about 222 nanometres by said unsaturated elastomeric interpolymer with a calibration curve generated, in the case of the analysis of butyl rubbers, from standard solutions of polyisoprene and, in the case of the analysis of ethylene-propylene-noconjugated diolefin rubbers, from standard solutions of the polymerized nonconjugated diolefin. The molecular weight distribution of the unsaturated elastomeric interpolymer is obtained by first calibrating the apparatus with a series of standards of known molecular weight and narrow molecular weight distribution. While it is preferable that the standards be of polymeric material that is very similar to the polymeric material being analyzed, in the event that such standards are not available, polystyrene standards such as these commercially available from Polymer Laboratories may be used. Since the molecular weights of the standards are known, a correlation between molecular weight and the time at which that particular weight produces a differential refractive index response can be obtained. Such a correlation can be utilized to determine the molecular weight distribution of the unsaturated elastomeric interpolymer. The absolute amount of antioxidant that is present in the unsaturated elastomeric interpolymer is determined by a comparison of the area under the graph resulting from the absorbance of ultraviolet radiation at about 275 nanometres to about 285 nanometres by said antioxidant with calibration curves generated from standard solutions of antioxidants that are used by commercial rubber producers to stabilize said unsaturated elastomeric interpolymers. Examples of said antioxidants are the sterically hindered phenol Irganox ® 1010, the phosphite Irgafos ® 168 and the substituted diphenylamine AgeRite ® Stalite S. Analysis of a mixture of said antioxidants according to the method of the present invention determined that the resolution of the individual antioxidants was satisfactory.

The following examples are intended to illustrate the invention and not to limit the invention. In the examples, unless otherwise specified, parts are by dry weight.

EXAMPLE 1

The amount of unsaturation in a number of commercially available butyl rubbers was determined according to the method of the present invention. First a series of standard solutions of synthetic natural rubber, Natsyn 2200, in tetrahydrofuran (THF) containing no preservative were prepared so that an equation for the relationship between the areas under the graphs and the mole percent unsaturation in butyl rubbers could be derived. The concentrations of these solutions are given in Table 1.

TABLE 1

| Sample # | Dilution | Concentration (W/V %) | Concentration (mole %)* |
|---|---|---|---|
| A |  | 20.8 | 17.78 |
| A1 | 5XA | 4.16 | 3.45 |
| A2 | 2XA1 | 2.08 | 1.72 |
| A3 | 2XA2 | 1.04 | 0.86 |
| B |  | 10.40 | 8.72 |
| B1 | 2XB | 5.20 | 4.30 |
| B2 | 2XB1 | 2.60 | 2.15 |
| B3 | 2XB2 | 1.30 | 1.07 |

Each standard solution was analyzed in triplicate using the following procedure. A 200 ul sample of the standard solution was injected into a Waters gel permeation chromatograph that was equipped with four columns connected in series. The first column was packed with Ultrastyragel ® having a pore size of $10^3$ angstrom, the second column was packed with Ultrastyragel ® having a pore size of $10^4$ angstrom, the third column was packed with Ultrastyragel ® having a pore size of $10^5$ angstrom and the fourth column was packed with Ultrastyragel ® having a pore size of $10^6$ angstrom. The Ultrastyragel ® in all four columns had a diameter of 5 microns. A Waters 481 ultraviolet detector connected in series with said gel permeation chromatograph was programmed to operate at 220 nanometres. Signals from said ultraviolet detector were digitized and fed to a computer which then generated a graph. The average areas under the graphs obtained are listed in Table 2.

TABLE 2

| Standard Solution | UV Absorbance Average Area under graph |
|---|---|
| A1 | 4917889 |
| A2 | 2530490 |
| A3 | 1273231 |
| B1 | 7004285 |
| B2 | 3469232 |
| B3 | 1721628 |

The average area under the graph from Table 2 and the mole percent value from Table 1 for each standard solution was used in a linear regression program to obtain an equation between area under the graph and mole percent unsaturation.

Y=0.6252X+0.07956
Y=mole percent unsaturation
X=area under the graph

Three different POLYSAR ® Butyl rubbers were each analyzed five times using the same procedure as that used for the analysts of the unsaturation standards and the amount of unsaturation in each sample calculated using the relationship derived above. The results of the analyses are given in Table 3. For comparison purposes, the amount of unsaturation in each sample was determined according to the method ASTM D 1541 (the iodine index method) and these results are also included in Table 3.

TABLE 3

| Sample # | Sample Weight (gm) | Average Area under graph |
|---|---|---|
| POLYSAR ® Butyl 402 | 0.0205 | 3373156 |
| POLYSAR ® Butyl 301 | 0.0202 | 2579429 |
| POLYSAR ® Butyl 100 | 0.0212 | 1456662 |
| | Mole % Unsaturation | Standard Deviation % |
| POLYSAR ® Butyl 402 | 2.14 | 1.4 |
| POLYSAR ® Butyl 301 | 1.67 | 3.3 |
| POLYSAR ® Butyl 100 | 0.94 | 0.5 |
| | Mole % Unsaturation ASTM D1541 | |
| POLYSAR ® Butyl 402 | 2.21 | |
| POLYSAR ® Butyl 301 | 1.65 | |
| POLYSAR ® Butyl 100 | 0.86 | |

From the above results it can be seen that there is a close correlation between the mole percent unsaturation obtained using the gel permeation chromatograph/ultraviolet detector method and the mole percent unsaturation determined using the iodine index method. The standard deviation on results obtained using the gel permeation chromatograph/ultraviolet detector method is about comparable to that obtained using the iodine index method but the former procedure is much simpler and more direct, not so tedious and not nearly as operator dependent.

EXAMPLE 2

The amount of unsaturation, the molecular weight distribution and the amount of antioxidant in a commercially available butyl rubber was determined according to the method of the present invention.

A solution of the butyl rubber containing a known weight of said butyl rubber in a measured volume of tetrahydrofuran (THF) containing no preservative was analyzed using the following procedure. A 200 ul sample of the solution was injected into a Waters gel permeation chromatograph that was equipped with three chromatographic columns which were connected in series and packed with a cross-linked polymeric material PL-GEL having a diameter of 10 microns and a mixture of pore sizes from $10^2$ to $10^6$ angstrom. A Waters 490 multichannel, multiwavelength ultraviolet detector programmed to operate at wavelengths of 220 nanometres and 280 nanometres and a Waters 410 differential refractive index detector were connected in series with said gel permeation chromatograph. Signals from said ultraviolet detector and said differential refractive index detector were digitized and fed to a computer which then generated graphs, the areas under which were proportional to the amount of unsaturation, the amount of antioxidant and the molecular weight distribution in the butyl rubber.

The equation relating peak area to mole percent unsaturation derived in Example I was used to calculate the mole percent unsaturation in the sample of butyl rubber.

A calibration curve for determining the molecular weight distribution of the butyl rubber was obtained using the following procedure. Eight polystyrene standards of known molecular weight and narrow molecular weight distribution were first analyzed in order to derive a calibration curve for polystyrene and then by means of the [Mark-Houwink coefficients for butyl rubber] a calibration curve for the butyl rubber was derived from the calibration curve for polystyrene.

The amount of antioxidant Irganox ® 1010 in the butyl rubber was determined by first analyzing a standard solution of the antioxidant and obtaining a response factor and then applying this response factor to the area under the graph generated in the analysis of the rubber.

The results of the analysis of the commercial butyl rubber are given in Table 4.

TABLE 4

| Sample | Sample Weight (gm) |
|---|---|
| POLYSAR ® Butyl 301 | 0.0207 |
| Unsaturation | |
| Average Area under Graph | Mole % Unsaturation |
| 4694843 | 1.68 |
| Antioxidant (Irganox ® 1010) | |
| Average Area under Graph | Mole % Irganox ® 1010 |
| 9383 | 0.14 |
| Molecular Weight Distribution | | |

| $M_w$ | $M_n$ | $M_w/M_n$ |
|---|---|---|
| 705968 | 147966 | 4.77 |

What is claimed is:

1. A method for determining the amount of unsaturation in an unsaturated elastomeric interpolymer of at least one monoolefin and one diolefin selected from the group consisting of butyl rubbers and ethylene-propylene-nonconjugated diolefin rubbers, said method comprising:

(i) dissolving a known weight of said unsaturated elastomeric interpolymer in a measured volume of a suitable solvent capable of dissolving said unsaturated elastomeric interpolymer and transparent to ultraviolet radiation down to about 217 nanometers;

(ii) passing a sample of the resulting solution through a gel permeation chromatograph in which three or more chromatographic columns comprise columns of porous particles of cross-linked polymeric material having a diameter of about 4 microns to about 11 microns and a pore size in the range of $10^2$ angstrom to $10^6$ angstrom, (iii) detecting the amount of unsaturation in said unsaturated elastomeric interpolymer as it is eluted from, the chromatographic column using an ultraviolet detector operated at a wavelength of about 217 nanometres to about 222 nanometres, and (iv) quantifying the amount of unsaturation.

2. A method according to claim 1, wherein the amount of unsaturation in said unsaturated elastomeric interpolymer is quantified by digitizing the output signals from the ultraviolet detector using a computer means and generating a graph in which the area under the graph for the amount of unsaturation in the unsaturated elastomeric interpolymer is proportional to its relative amount.

3. A method according to claim 2, wherein said amount of unsaturation in the unsaturated elastomeric Interpolymer content of the eluant is quantified and compared to a calibration curve.

4. A method according to claim 1, wherein said chromatographic columns comprise four chromatographic columns of porous particles of cross-linked polymeric material having a diameter of about 4 microns to about 6 microns, connected in series, said porous particles in the first column having a pore size of about $10^3$ angstrom, said porous particles in the second column having a pore size of about $10^4$ angstrom, said porous particles in the third column having a pore size of about $10^5$ angstrom, and said porous articles in the fourth column having a pore size of about $10^6$ angstrom.

5. A method according to claim 1, wherein said chromatographic columns comprise three chromatographic columns of porous particles of cross-linked polymeric material having a diameter of about 4 microns to about 6 microns and a pore size in the range of $10^2$ angstrom to $10^6$ angstrom, connected in series.

6. A method according to claim 1, wherein said solvent is selected from the group consisting of tetrahydrofuran that does not contain preservative, cyclohexane, and hexane.

7. A method according to claim 1, which further comprises the simultaneous detection and quantification of the antioxidant content of said unsaturated elastomeric interpolymer and the molecular weight distribution of said unsaturated elastomeric interpolymer as said antioxidant and said unsaturated elastomeric interpolymer are eluted from said chromatographic columns.

8. A method according to claim 7, wherein the amount of unsaturation in said unsaturated elastomeric interpolymer and the amount of antioxidant are detected as said unsaturated elastomeric interpolymer and said antioxidant are eluted from the chromatographic columns using a multichannel, multiwavelength ultraviolet detector operated at about 217 nanometers to about 222 nanometres and about 275 nanometers to about 285 nanometers and the molecular weight distribution of said unsaturated elastomeric interpolymer is determined as said unsaturated elastomeric interpolymer is eluted from said chromagraphic columns using a differential refractive index detector connected in series with said multichannel, multiwavelength ultraviolet detector.

9. A method according to claim 8, wherein said chromatographic columns comprise three chromatographic columns of porous particles of cross-linked polymeric material having a diameter of about 4 microns to about 6 microns and a pore size in the range of $10^2$ angstrom to $10^6$ angstrom, connected in series.

10. A method according to claim 8, wherein the amount of unsaturation in said unsaturated elastomeric interpolymer, the amount of antioxidant and the molecular weight distribution of said unsaturated elastomeric interpolymer are quantified by digitizing the output signals from the ultraviolet detector and the differential refractive index detector using a computer means and generating graphs in which the areas under said graphs for the amount of unsaturation in the unsaturated elastomeric interpolymer, the amount of antioxidant and molecular weight distribution of said unsaturated elastomeric interpolymer are proportional to their relative amounts.

11. A method according to claim 8, wherein said amount of unsaturation in the unsaturated elastomeric interpolymer, said amount of antioxidant and said molecular weight distribution of the unsaturated elastomeric interpolymer are quantified and compared to calibration curves.

12. A method according to claim 9, wherein said solvent is selected from the group consisting of tetrahydrofuran without preservative, cyclohexane, and hexane.

* * * * *